United States Patent [19]

Obiaya

[11] 4,128,458
[45] Dec. 5, 1978

[54] COMBUSTIBLE ELEMENT AND OXYGEN CONCENTRATION SENSOR

[76] Inventor: Joseph O. Obiaya, 4773 Walford, #13, Warrensville Heights, Ohio 44128

[21] Appl. No.: 845,049

[22] Filed: Oct. 25, 1977

[51] Int. Cl.² ............................................. G01N 27/46
[52] U.S. Cl. .............................. 204/1 T; 204/195 S; 422/94; 422/98
[58] Field of Search ............................ 204/1 S, 195 S; 23/254 E, 255 E, 232 E; 73/23, 25, 26, 27 R

[56] References Cited

U.S. PATENT DOCUMENTS

| | | | |
|---|---|---|---|
| 3,546,086 | 12/1970 | Sayles | 204/195 S |
| 3,595,621 | 7/1971 | Andreatch | 23/254 E |
| 3,620,931 | 11/1971 | Reichner | 204/195 S |
| 3,676,820 | 7/1972 | Taguchi | 23/254 E |
| 3,720,594 | 3/1973 | Wilson | 204/195 S |
| 3,791,936 | 2/1974 | Pebler et al. | 204/195 S |
| 3,960,500 | 6/1976 | Ross et al. | 204/1 S |
| 3,981,785 | 9/1976 | Sandler | 204/1 S |
| 4,013,943 | 3/1977 | Chou et al. | 23/254 E |

Primary Examiner—T. Tung

Attorney, Agent, or Firm—Watts, Hoffmann, Fisher & Heinke Co.

[57] ABSTRACT

Apparatus and method are claimed for determining the oxygen and combustible element concentration in a sample gas. In the preferred embodiment the sensor includes an analyzing block with conduits for separately routing a sample gas past a combustible element analyzer and an oxygen analyzer. The oxygen analyzer utilizes a voltaic reaction in a solid electrolyte to correlate the oxygen concentration to the voltage produced by the voltaic reaction. The combustible analyzer induces an exothermic reaction in the region of a thermopile to produce a voltage difference along the length of the thermopile bearing a functional relationship to the concentration of a combustible element in the exothermic reaction. The conduit for routing the gas past the combustible element analyzer includes a heating labyrinth for raising the temperature of the sample and a port for accessing air to be mixed with the sample. Also included in this combustible analyzer conduit is a pressure sensing device for maintaining proper calibration regardless of sample flow rate. The flow within the block is maintained by an aspirator operated by a pressure regulated compressed air source.

11 Claims, 7 Drawing Figures

COMBUSTIBLE ELEMENT AND OXYGEN CONCENTRATION SENSOR

BACKGROUND AND SUMMARY OF THE INVENTION

This invention relates to an improved apparatus and technique for determining combustible and oxygen concentration in a combustible fuel environment. By monitoring both the concentration of the oxygen and the concentration of the combustible it is possible to maintain an environment in which the most efficient burning of the combustible is achieved.

To appreciate the usefulness of the invention one must understand the details of the combustion process. By way of example, it is useful to examine the combustion (or oxidation) of carbon monoxide in an oxygen environment. Tow molecules of carbon monoxide react with one molecule of oxygen to yield two molecules of carbon dioxide plus a given amount of heat. The most efficient burning of the carbon monoxide occurs when the ideal stoichiometric ratio of two moles of carbon dioxide is burned in one mole of oxygen. If either the carbon monoxide concentration exceeds or is less than this ideal relationship, the burning is inefficient.

Consider an example where the carbon monoxide concentration exceeds the ideal situation. In this instance the excess carbon monoxide tends to inhibit the combustion process. If the carbon monoxide concentration is too high, the burning may become extinguished and the reaction may need to be restarted. If, during this restart process, oxygen concentration is accidentally increased, there may result a spontaneous energy release which may be destructive.

In the opposite situation where the carbon monoxide concentration decreases from the optimum level, there is an excess of oxygen for the amount of carbon monoxide present in the system. Under those circumstances, energy efficiency is lost in heating the excess oxygen (or air) in the system. Thus for safety and for cost efficiency reasons, it would be preferable to maintain carbon monoxide and oxygen concentrations at the optimum level.

From the above examples it would seem readily apparent that the optimum situation is achieved in which both the oxygen and the carbon monoxide concentration of the fuel can be monitored during the combustion process to assure that the levels of each remain in approximately the correct stoichiometric concentrations.

To the knowledge of the present inventor, the prior art discloses no unitary apparatus for scientifically determining the relative concentrations of both the oxygen and the combustible constituents of a fuel mixture continuously in a harsh industrial environment containing sulfur dioxide. U.S. Pat. No. 3,960,500 to Ross et al discloses a technique and apparatus for determining the oxygen concentration of a gas sample. However, it is apparent that not only the oxygen concentration but also the combustible concentration is necessary to determine whether the necessary stoichiometric relationship exists between the two.

It is the purpose of the present invention to meet this prior art deficiency in a mamnner which enables the determination experimentally of the relative concentrations of not only the oxygen but also the combustible continuously in the burning environment. The present invention achieves this capability by sampling the gaseous environment and routing this sample through a conduit means which divides the sample into three portions. A common aspirator or eductor is utilized to cause a pressure drop in this conduit, which causes the sample to flow into the three portions and thereby causes it to flow past two sensors.

One of the sensors is an oxygen analyzer and the other is a combustibles analyzer. The oxygen analyzer uses a voltaic reaction in a zirconium oxide crystal structure doped with certain predetermined impurities to determine the percentage concentration of oxygen molecules in the gas sample. The combustibles analyzer utilizes a thermopile technique for determining the concentration of combustible element within the sample. Since the combustibles analyzer of the present invention operates at an elevated temperature, the conduit portion routing this sample includes a labyrinth heater with surfaces that radiate heat to the sample before its concentration is analyzed. In the example noted previously, it is possible for this combustible element analyzer to determine the concentration of carbon monoxide in the sample routed through it. By monitoring the concentrations obtained from these two devices, it is possible for the system user to adjust the combustible and oxygen environment until the sensors indicate that the concentrations are at or near the optimum levels. This real time monitoring of combustible and oxygen concentration results, therefore, in considerable cost savings, safety, and increased efficiency in the combustion system.

The above and other features and advantages of the invention will become more apparent as the invention becomes better understood from the detailed description that follows, when considered in connection with the accompanying drawings.

DETAILED DESCRIPTION

Figure 1:
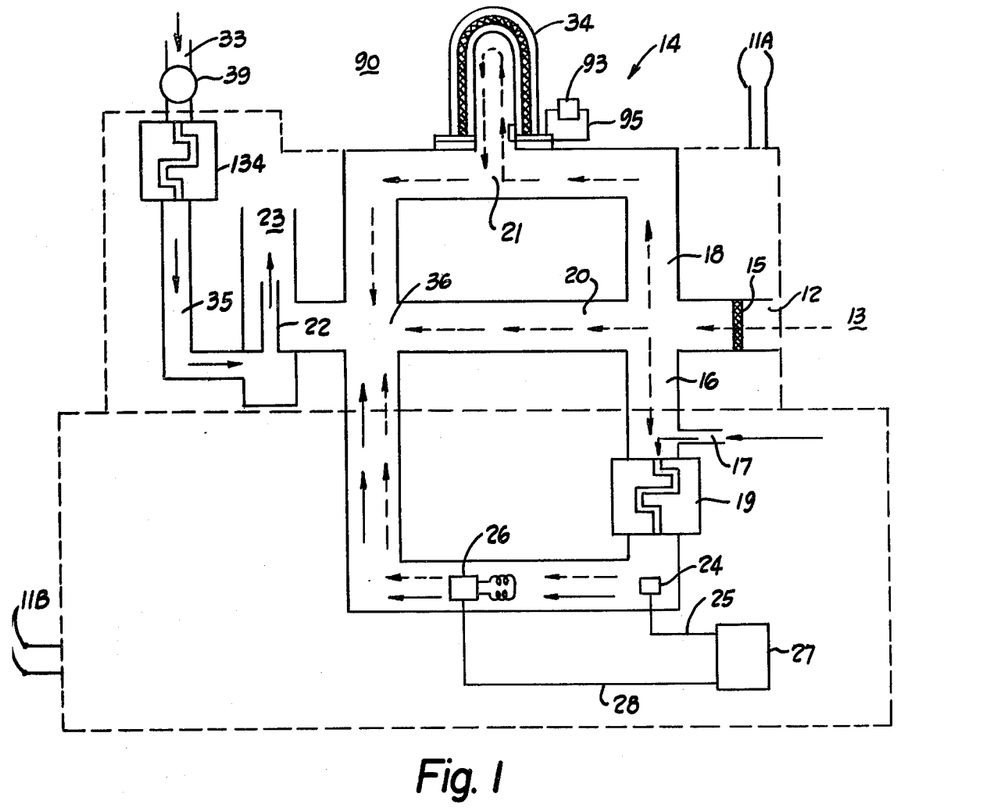
FIG. 1 is a schematic diagram of an oxygen concentration and combustible element concentration analyzing system embodying the present invention.

FIG. 1 presents a general schematic diagram of an oxygen concentration and combustible concentration analyzer comprising an inlet 12 for obtaining a sample of gas from a furnace or other sampling area 13, a conduit system 14 which divides into three portions 16, 18, and 20, and an outlet port 23 into which the three portions merge. Fluid flow within the conduit system 14 is maintained by means of an aspirator or eductor 22 located adjacent the outlet port. This configuration allows the gas to flow through the respective conduit portions, be analyzed by analyzers 26, 34 within the respective portions 16, 18, and be recombined and emitted from the outlet port 23.

The gaseous portion entering the conduit portion 16 will be tested for its combustible element content. It is combined with atmospheric air at an air inlet 17 in the conduit portion 16 and the combined flow then enters a heating labyrinth 19 which transfers ambient heat to the flow. After being heated in the labyrinth to a temperature of approximately 400° F., the gases comprising this portion of the sample are emitted from the heating labyrinth 19 and pass a pressure transmitter 24 which helps maintain proper calibration of the analyzer 26. After leaving the general area of the pressure sensor, the part of the sample passing through conduit portion 16 is tested by the combustible concentration analyzer 26 and is then recombined with the other portions of the gaseous sample.

A second portion of the gas sample to be analyzed by this system enters conduit portion 18 and travels along that conduit portion until it reaches an area 21 where the oxygen concentration analyzer 34 is located. A part of that sample gas enters the oxygen concentration analyzer 34 and travels along a generally U-shaped path until it again joins conduit portion 18. While within this confined area, a portion of oxygen within the gaseous sample interacts with the analyzer to produce an electrical output indicative of the oxygen concentration. The second sample portion then continues to travel along conduit portion 18 until it is reunited with the other gaseous elements.

The third conduit portion 20 serves to carry a third portion of the sample gas to the juncture 36 where the flows are recombined. This conduit facilitates gas flow and eliminates undesirable pressure variations within the system.

After reuniting at the juncture 36, the gases are swept from the system by the aspirator 22. Since the details of the aspirator are not part of this invention, it has been presented in the schematic form and may be one of a number of commercially available devices to produce the desired result. After analysis has been completed the sample is returned to the original source.

A final conduit 33 enters the system 14 to provide a source of compressed air to the aspirator 22. The compressed air passes through a pressure regulator 39 to maintain constant pressure in conduit 35 thereby insuring uniform aspirator operation. Uniform aspirator functioning results in uniform sample flow within the system 14 and uniform sample and air flow within the combustible conduit 16, which are necessary for proper sensor calibration. The air is heated within a labyrinth heater 134 and passes through conduit 35 to the aspirator 22. If unheated compressed air is used in conduit 35 moisture condenses at the outlet port 23. Such condensation attracts dirt and dust particles which may clog the outlet port and interrupt sample flow through the system.

The entire conduit system 14 is heated to a temperature of 400° F. by block heater elements 11A and 11B. The precise mechanism for heating the system 14 to this level is not critical and can be accomplished in any commercially reasonable manner.

The laybrinth 19 of the combustible element analyzing portion of the system serves to transfer heat to the sample gas after it has been combined with a quantity of air at atmosphere pressure introduced through the inlet 17. In a preferred construction the labyrinth is either cast or machined to form an integral part of the combustible sample conduit path 16. The attainment of a 400° F. temperature of the gas is crucial in producing a catalytic reaction on the individual sensors of the combustibles analyzer, and since the sensor response is dependent upon the sample temperature, a reliable means of heating the sample fluid to a predetermined temperature within the system is a necessity. By including the labyrinth as a direct part of the combustible sample flow path, a reliable constant temperature of the sample can be assured by the ambient temperature of the labyrinth, which will facilitate calibrating the system. Passage of the sample through the labyrinth is an effective way to obtain final temperature of 400° F. After leaving the labyrinth 19 the sample passes the pressure sensor 24 and enters the region of the combustible concentration analyzer 26.

Figure 2:
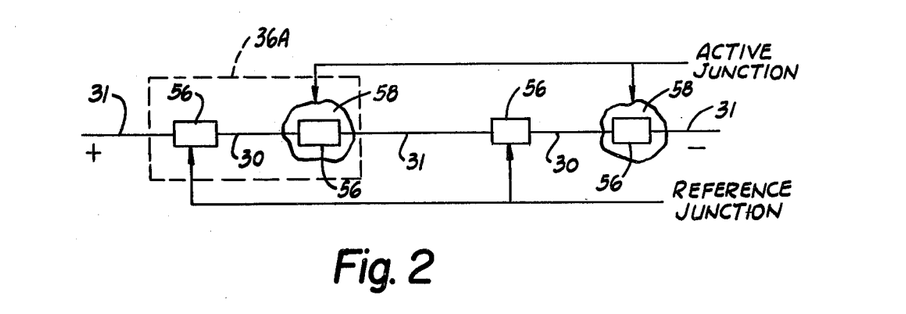
FIG. 2 is a schematic diagram of a number of series connected thermocouples (thermopile) for a combustible element analyzer.

As seen schematically in FIG. 2, the combustible concentration analyzer 26 comprises a number of series-connected thermo-couples 36A sensitive to temperature changes at their metallic junctions. This connection of thermo-couples forms a matrix arrangement (thermopile) whose shape can be varied. Each of the thermo-couples comprises a chromel element 30 and an alumel element 31 which are joined at junctions 56. While chromel and alumel have been chosen in the preferred embodiment of the invention other dissimilar metals can be chosen to form the thermo-couple. For example a segment of platinum could be joined to a segment of 90% platinum and 10% rhodium to produce the required effect. Also other percentages of the platinum-rhodium alloy could be chosen. At a chromel-alumel junction any temperature variation above the ambient temperature of the rest of the configuration will produce a current flow within the arrangement. To transform the chromel-alumel series connected thermo-couples into a combustible element analyzer, a platinum element 58 (see FIG. 20) which is a paste is coated upon alternate junctions. The platinum coated junction is referred to as an active or catalytic junction and the non-coated junction as a reference or non-catalytic junction.

The platinum element 58 induces an exothermic reaction within the combustible concentration analyzer. Platinum was chosen for two reasons; (a) the platinum will effectively catalyse a reaction between oxygen and a combustible element within the system when a high enough ambient temperature is maintained, and (b) the platinum catalyst element effectively withstands any degradation due to the presence of unwanted foreign elements which enter the system with the sample gas. For example, the platinum catalyst element is especially resistent to the poisonous effects of sulphur dioxide ($SO_2$) at elevated temperature above 800° F. With the platinum catalyst element in place the chromel-alumel pairs in combination with their crimping elements and the catalyst complete the construction of the matrix arrangement. While the platinum paste is preferred due to its operating characteristics in an environment with high sulfur dioxide concentrations, other substances such as a palladium paste can be used to catalyse the reaction.

Figure 3:
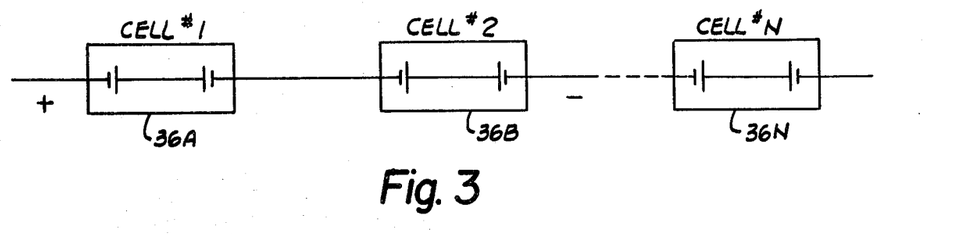
FIG. 3 is a diagram showing the functional equivalence between series connected thermocouples and series connected batteries.

As seen in FIG. 3, the combination of the series connected thermo-couples the catalytically induced exothermic reactions produces an effect similar to a series connection of batteries. Every active-reference junction pair can be thought of as an individual cell 36A, 36B and 36N which produces a voltage difference within the series connected system. With reference to FIGS. 2 and 3, the configuration of the chromel-alumel pairs depicted indicates a voltage increase from right to left.

Each succeeding active-reference pair produces a voltage difference due to the exothermic reaction occuring at the active junction. The total system output from this configuration can be found by summing the individual voltage differences on the thermo-couple connections. As seen in FIG. 3 this would be equivalent to N times the voltage difference from one active-reference pair.

Reversing the order of the chromel 30 alumel 31 pairs in the sensor causes the electrical polarity of the system to reverse. If in FIG. 2 the chromel elements 30 were changed to alumel 31 and vice versa the voltage would increase from left to right. The sequence depicted in FIG. 3 is preferable, however, due to improved signal to noise ratio of that configuration.

Figures 4, 5:
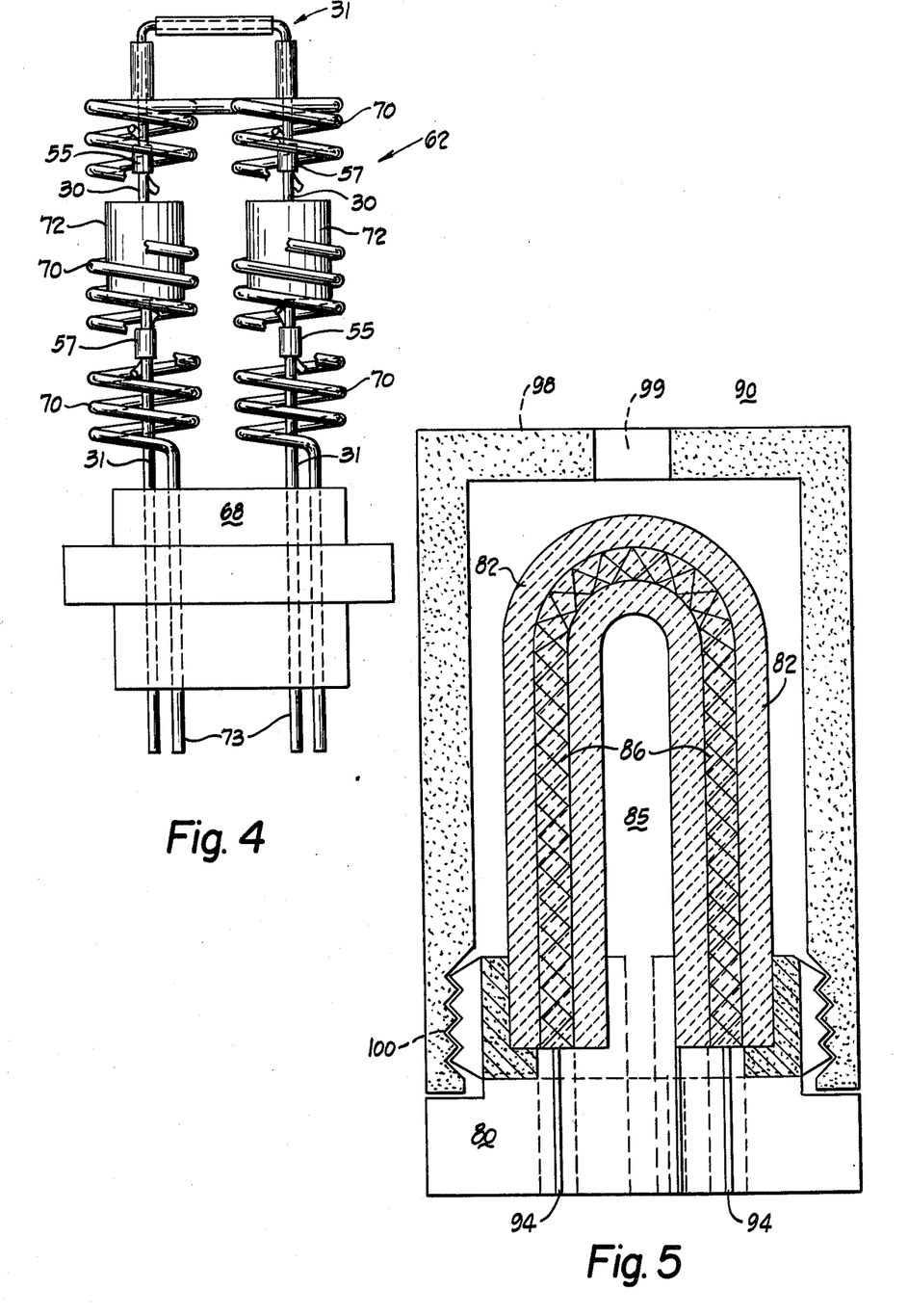
FIG. 4 depicts a functional combustible element analyzer formed by crimping together discreet thermocouple elements.
FIG. 5 is a sectional view of an improved oxygen concentration analyzer.

One arrangement of the thermo-couple configured combustible analyzer is shown in FIG. 4. this analyzer comprises a base 68 and a series of connected thermo-couples 62 arranged in a U-shaped configuration. Mechanically, links of alumel and chromel are held together by a series of crimp materials 55 and 57 placed around the chromel-alumel elements to form a junction. In the present arrangement the crimp for a reference junction 55 is made of silver and the crimp for an active junction 57 made of platinum.

In the system shown in FIG. 4, a platinum catalyst material 58 (shown only in FIG. 2) is applied to alternate crimp junctions 57 within the system. In order to raise the ambient temperature of the thermo-couples to a range of approximately 800° F. (i.e. 400° F. higher than the sample entering the combustible sensor) a series of heating coils 70 are arranged coaxially with the thermo-couple series connections. These heater coils are connected to a source of voltage and due to joule heating cause a rise in the ambient temperature surrounding the junctions. The 800° F. operating temperature is desirable primarily to eliminate $SO_2$ poisoning of the catalyst element 58. Since the heating elements are connected to a source of electrical energy, it is necessary that they be insulated electrically from the thermopile conduction matrix. For this reason a bead-like element 72 is imposed between the heater coils and the thermo-couple junctions. This element can be of any suitable material which will conduct heat while insulating the elements from electrical contact. In the preferred embodiment this bead insulation material is mullite and is bound to the heating coils 70 by a suitable contact cement.

The electrical leads to both the thermo-couple matrix and the heater coils 70 pass through the base 68 to a standard electrical pin connector 73 to achieve electrical insulation of the output signal of the combustion concentration analyzer from the heat coil.

Figure 6:
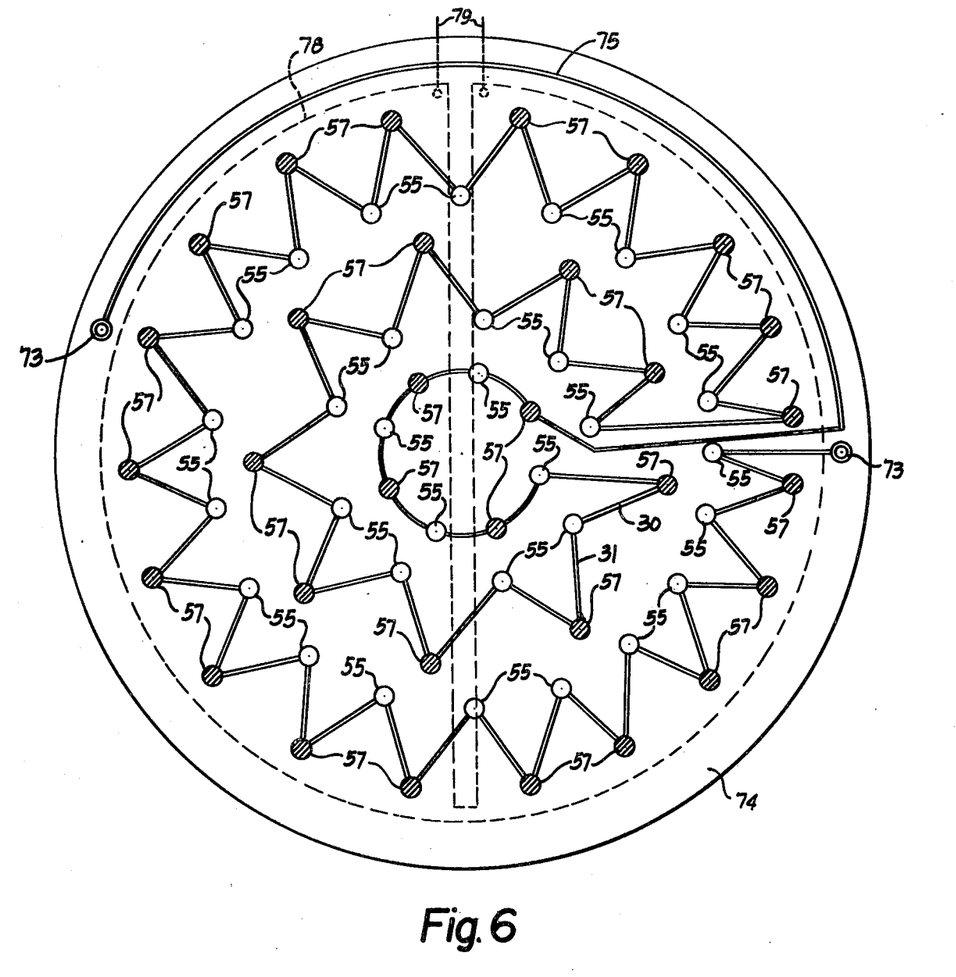
FIG. 6 is a plan view of a combustible element analyzer constructed using a sputter-etch technique which provides improved sensitivity readings.

A second version of the combustible element analyzer is shown in FIG. 6. This apparatus works on the same principal as that of FIG. 4 but possesses certain attributes which are superior. As seen in FIG. 6, a number of chromel 30 and alumel 31 pairs are sputter-etched in the form of a thermopile matrix. The alternating active junctions 57 of these pairs are coated with a catalyst material 58 which produces the exothermic reaction in a similar manner to the pior noted device. The difference between the two is the physical construction and fabrication technique involved. The analyzer of FIG. 6 is comprised of layers coated upon a substrate material 74. Through the use of a masking technique similar to those used in integrated circuit fabrication, the chromel-alumel and catalyst elements are successively sputter-etched onto the substrate material at desired locations to form an operating thermopile matrix of thermo-couples. The precise order and configuration of the chromel-alumel and catalyst etching are not critical to system performance. The electrical interconnection circuit 75 is also sputtered onto the substrate material 74 in a pattern to connect the thermo-couple matrix to the connections 73. As in the arrangement of FIG. 4, it is necessary to again raise the temperature of the ambient conditions surrounding the chromel-alumel pairs to approximately 800° F. To attain this temperature, a resistance heating circuit 78 shown in phantom comprising a resistive element has been sputter-etched upon the substrate on the surface opposite to the combustible analysis matrix. In this way electrical insulation is readily obtained between the thermopile and contacts 79 to the heating circuit and as long as the substrate material is a good conductor of heat the ambient temperature surrounding the junctions 55 and 57 necessary for preventing $SO_2$ poisoning effect is achieved.

By using the masking fabrication process to produce the construction of FIG. 6, it is possible to achieve combustible concentration analyzer uniformity and increased production capabilities. It should also be noted that the increased number of alumel-chromel junctions increases the insensitivity to the point that even low levels of combustible concentration produce large enough signals for analysis.

The two combustible concentration analysis devices of FIGS. 4 and 6 produce a voltage at their pin connections 73 which is directly proportional to the concentration of the combustible in the sample gaseous fluid. This relationship follows from the functional correlation between heat given off and combustible concentration present at the active junctions. The voltage from the pin connections 73 of the matrix is then calibrated to yield the combustible element concentration. This calibration is done by utilizing a gas of known concentration to obtain reference readings upon a suitable volt meter 27. (see FIG. 1). These reference readings and the proportional relation between voltage and concentration allows interpolation to other concentration values. Since the particular reading device utilized is variable and not an element of the present invention, details of this calibration technique have been omitted.

As seen in FIG. 1, the design of the present system includes a filter or guard 15 which helps eliminate foreign elements such as dirt and unwanted particles which could adversely affect the operation of the total system. For industrial application where the gas carries particulate water or dirt, it has been found that the filter tends to clog with particles and a reduced flow rate within the conduit system 14 results due to reduced pressure differences along the system. If, for example, dirt and other elements within the sample environment cause the filter element to clog, the pressure variations from one portion of the conduit to the other vary to a lesser degree. This reduced pressure drop results in a reduced flow rate of the combustible sample past the combustible sample element analyzer 26 and adversely affects the system calibration. If, for example, the amount of combustibles passing by the analyzer 26 per unit time is reduced, fewer reactions can take place along the matrix thereby indicating a lower combustion concentration. This happens when, in fact, the combustible concentration has remained unchanged, and only the flow rate within the conduit 16 has been altered. To take into account the change in flow rate, a pressure sensor 24 has been introduced within the combustible analysis conduit 16.

The pressure transmitter 24 is one of a number of commercially available devices which sense changes in pressure. Attached to the pressure transmitter is an electrical interconnect 25 which transmits the output from the device 24 to the voltmeter 27. When the output from the pressure transmitter 24 is added to the combustible concentration analyzer output 28, a reading is produced that compensates for reduced flow rate due to the environment in which this system must operate. By way of example, if one uses a pressure transmitter which produces a voltage reading directly proportional to the pressure drop, one can add the output from this device interconnect 25 to the combustible concentration analyzer output interconnect 28 to produce a signal whose voltage is independent of flow rate within the conduit. Thus it is apparent that the system can be calibrated using one flow rate, but by utilization of a pressure sensor, will be accurate for all flow rates within the sensing capabilities of the combustion analyzer.

The upper conduit portion 18 in FIG. 1 provides a channel for the sample gas to be routed for oxygen concentration analysis. The sample gas flows through the upper conduit to the oxygen sensor 34. The oxygen sensor comprises a U-shaped or closed-end tubular member which forms a chamber 85 (see FIG. 5) within which the sample gas is allowed to flow. A base 80 serves as a support mount for an oxygen sensor heater element 86 that is in the form of a grid and mesh construction. Interwoven and layered upon opposite sides of the heater element 86 is a crystal-type structure of zirconium oxide 82.

Functionally the oxygen concentration sensor operates usng a voltaic reaction which involves the transfer of chemical energy into electrical energy. The zirconium oxide 82 is doped with a bivalent molecule such as magnezia, yttria, calcia to produce vacancies of minus 2 valence oxygen ions 87 (FIG. 7) within the crystal structure of the zirconium oxide.

Figure 7:
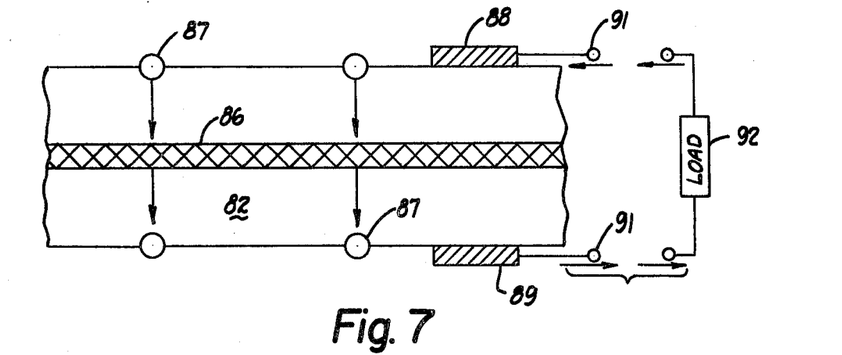
FIG. 7 is a schematic diagram showing oxygen ion migration within the oxygen concentration analyzer.

By the use of platinum electrodes 88 and 89 (see FIG. 7) on opposite zirconium oxide surfaces one can induce a chemical reaction within the zirconium oxide (assuming proper ion concentration due to doping). The reaction at the cathode follows the relation:

and at the anode:

In the present invention the anode electrode 89 is in contact with the sample gas within the chamber 85 and the cathode electrode 88 is in contact with the surrounding atmosphere 90 which acts as a source of known oxygen concentration. If an external load circuit 92 is attached to the electrodes, the combination of the two half cell reactions at the cathode and anode cause oxygen ion migration and therefore a current to flow within the circuit.

The voltage created by this reaction is given by the Nernst equation:

$$E = \frac{RT}{nF} \ln \frac{P_r}{P_s}$$

where
$R =$ Universal Gas Content
$F =$ Faraday's Number
$T =$ Absolute Temperature
$P_r =$ Oxygen Partial Pressure of reference gas.
$P_s =$ Oxygen Partial Pressure of sample gas.
$n$ number of electrons transferred in half cell equation.

Since the oxygen concentration of the surrounding atmosphere 90 is known, its partial pressure can be determined if atmospheric pressure is known. The voltage difference at a pair of electrode connections 91 can be measured by use of a suitable voltmeter 93 substituted in place of the load circuit 92. By combining this information with the other components of the Nernst equation, oxygen partial pressure in the sample can be calculated and through knowledge of the sample pressure the percent oxygen concentration calculated. Alternatively, knowledge that the voltage difference at the electrodes 88 and 89 is proportional to $\ln (1/P_s)$ enables the user to calibrate a suitable voltmeter by using a sample of known oxygen concentration.

The voltaic reaction occuring in the oxygen sensor is sensitive to temperature conditions. The most suitable lattice structure and ion concentration within the zirconium oxide occurs at approximately 1500° F. The present invention utilizes a heater element 86 directly embeded within the zirconium oxide 82. The zirconium oxide is coated to the heater and extends around and through the mesh structure as seen in FIG. 5. This configuration facilitates ion flow within the doped zirconium oxide directly through the heater element 86. The heater element therefore gives structure to the zirconium oxide element without disrupting its well-defined crystal lattice structure. The element 86 is energized by power connections 94 and may be either A.C. or D.C. operated. Care must, of course, be taken to inusre that the power connections 94 to the heater 86 are electrically insulated from the conductors 95 leading from the oxygen sensing electrodes 88 and 89 to the voltmeters 93. Surroundng the oxygen analyzer 34 is an insulation guard 98 as seen in FIG. 5. This guard screws onto the base 80 by means of a threaded coupling 100 and includes an opening 99 for receiving air from the surrounding atmosphere 90. The guard insures against excessive heat loss and therefore is made of appropriate heat insulating material.

After the oxygen concentration sample has been tested it returns to the oxygen conduit 18 and recombines with the samples from the other conduits 16 and 20 before being ejected out the outlet 23.

While the present invention has been described with particularity, it should be understood that various modifications and alterations may be made therein without departing from the spirit and scope of the invention set forth in the appended claims.

What is claimed is:
1. A combustible fluid and oxygen concentration sensor comprising:
 a. a combustible concentration analyzer;
 b. an oxygen concentration analyzer;

c. conduit means for routing a fluid sample past said combustible concentration analyzer and oxygen concentration analyzer;
d. an inlet port to said conduit means for receiving a sample fluid;
e. an outlet port from said conduit means for ejecting said sample after analysis;
f. means for producing fluid flow in said conduit means from said inlet port to said outlet port;
g. means to connect the combustible concentration analyzer to an indicator; and
h. means to connect the oxygen analyzer to a second indicator;
i. said conduit means comprising:
   i. first and second portions arranged to divide the flow into separate paths downstream from said inlet and upstream from said flow producing means;
   ii. said first portion supplying the oxygen analyzer but not the combustible analayzer with sample fluid;
   iii. said second portion supplying the combustible analyzer but not the oxygen analyzer with sample fluid;
   iv. a heater associated with said second portion upstream of said combustible analyzer; and
   v. an inlet for providing air to said second portion upstream of said heater, to insure complete combustible analysis within said combustible analyzer.

2. The combustible fluid and oxygen concentration sensor of claim 1 wherein said flow producing means comprises an aspirator for producing a pressure variation within said conduit means and wherein said conduit means further comprises a compressed air conduit portion for routing a source of compressed air to said aspirator.

3. The combustible fluid and oxygen concentration sensor of claim 2 wherein said heater comprises a winding labyrinth arrangement forming a part of said second conduit portion.

4. The combustible fluid and oxygen concentration sensor of claim 3 including means for filtering the fluid flowing through said conduit portions, and a pressure sensing means associated with said second conduit portion for sensing the pressure therein and for producing a signal indicative of the pressure; said pressure sensing means including connection means for sending the signal to the indicator for adjusting calibration of the indicator in response to pressure variations in said second conduit portion.

5. The combustible fluid and oxygen concentration sensor of claim 4 where the combustible concentration analyzer comprises:
a. means including a plurality of bi-metallic thermocouples connected in series and forming a thermopile for sensing the temperature at each thermocouple and producing voltage differences along the length of the thermopile;
b. a catalyst associated with alternating junctions of said thermocouples to induce exothermic reactions at said alternating junctions with a combustible and thereby induce a voltage gain; and c. means to electrically connect said thermopile to an indicator sensitive to said voltage for indicating the concentration of combustibles adjacent said series.

6. The combustible fluid and oxygen concentration analyzer of claim 4 where said oxygen concentration analyzer comprises;
a. a reactor member;
b. a heater element embedded within said reactor member; and
c. a base for mounting said reactor member;
d. said reactor member comprising:
   i. an electrolyte with oxygen ion vacancies providing paths for oxygen ion conduction;
   ii. a first and second conductive electrode for inducing a voltaic reaction within said source, and
   iii. means for connecting said first and second conductive electrodes to external means for measuring the voltage difference created in said electrodes by said voltaic reaction.

7. The combustible fluid and oxygen concentration sensor of claim 2 where said sensor further comprises a regulator for maintaining constant pressure in said compressed air conduit, thereby insuring uniform aspirator functioning to provide uniform sample and air flow.

8. The combustible fluid and oxygen concentration sensor of claim 7 wherein the sensor includes a labyrinth heater inserted in the compressed air conduit to reduce moisture condensation at the outlet port.

9. A method for determining the oxygen concentration and combustible element concentration of a sample gaseous fluid comprising the steps of;
a. obtaining a sample of gas to be analyzed;
b. causing said sample to flow through a conduit block heated to a constant ambient level;
c. dividing said sample into first and secpond portions;
d. routing the second portion past an air inlet port in said block and obtaining excess air to be mixed with said second portion;
e. routing said second portion and excess air past a combustible analyzer for determining the combustible elememt concentration of said second portion;
f. routing the first portion past an oxygen concentration analyzer for determining the oxygen concentration of said first portion; and
g. recombining said first and second portions downstream from said analyzer and causing them to be ejected from said conduit block from an exhaust port.

10. The method of claim 9 which further comprises the steps of:
a. routing said second portion through a labyrinth heater thereby insuring said portion reaching said ambient level; and
b. inserting a pressure sensing device in said conduit block and obtaining a measure of sample flow thereby insuring proper combustible analyzer calibration regardless of flow rate.

11. The method of claim 9 where said sample flow is achieved by inserting a compressed air operated aspirator near the exhaust port and obtaining uniform aspirator operation by regulating the pressure of the compressed air operating said aspirator.

* * * * *

REEXAMINATION CERTIFICATE (591st)

United States Patent [19]

Obiaya

[11] B1 4,128,458

[45] Certificate Issued  Nov. 18, 1986

[54] COMBUSTIBLE ELEMENT AND OXYGEN CONCENTRATION SENSOR

[76] Inventor: Joseph O. Obiaya, 4773 Walford, #13, Warrensville Heights, Ohio 44128

Reexamination Request:
No. 90/000,449, Sep. 26, 1983

Reexamination Certificate for:
Patent No.: 4,128,458
Issued: Dec. 5, 1978
Appl. No.: 845,049
Filed: Oct. 25, 1977

[51] Int. Cl.⁴ ............................................. G01N 27/46
[52] U.S. Cl. ................................. 204/427; 204/410; 204/428; 422/94; 422/98
[58] Field of Search ................... 204/15, 421–429, 204/408–410; 136/225, 230

[56] References Cited

U.S. PATENT DOCUMENTS

| | | | |
|---|---|---|---|
| 1,321,063 | 11/1919 | Lamb et al. | 436/147 |
| 1,640,801 | 8/1927 | Petersen . | |
| 2,234,128 | 3/1941 | Miller | 436/152 |
| 2,531,592 | 11/1950 | Yant et al. | 436/134 |
| 2,743,167 | 4/1956 | Cherry | 422/93 |
| 2,814,952 | 12/1957 | Ryant . | |
| 3,546,086 | 12/1970 | Sayles | 204/195 S |
| 3,595,621 | 7/1971 | Andreatch | 23/254 E |
| 3,620,931 | 11/1971 | Reichner | 204/195 S |
| 3,676,820 | 7/1972 | Taguchi | 23/254 E |
| 3,720,594 | 3/1973 | Wilson | 204/195 S |
| 3,791,936 | 2/1974 | Pebler et al. | 204/195 S |
| 3,960,500 | 6/1976 | Ross et al. | 204/1 S |
| 3,981,785 | 9/1976 | Sandler | 204/1 S |
| 4,013,943 | 3/1977 | Chou et al. | 23/254 E |
| 4,063,898 | 12/1977 | Fisher . | |
| 4,129,491 | 12/1978 | Obiaya | 204/410 |
| 4,141,955 | 2/1979 | Obiaya | 136/225 |

FOREIGN PATENT DOCUMENTS

970434 9/1964 United Kingdom ............... 204/409

OTHER PUBLICATIONS

Publication "Engineering Specification E65-11, Gas Sampling System and Accessories, 1970".
Bulletin P-23 of Thermox Instruments, Inc., 1976.
Publication "Product Specification E65-1, Oxygen and Combustible Analyzer", 1956.
Publication "Bailey Product Instructions E65-6, Gas Analyzers Type OA, OB and OC, 1965".
Publication, "Product Instruction, E65-15, Heat Prover Combustible Analyzer" 1956.

*Primary Examiner*—T. Tung

[57] ABSTRACT

Apparatus and method are claimed for determining the oxygen and combustible element concentration in a sample gas. In the preferred embodiment the sensor includes an analyzing block with conduits for separately routing a sample gas past a combustible element analyzer and an oxygen analyzer. The oxygen analyzer utilizes a voltaic reaction in a solid electrolyte to correlate the oxygen concentration to the voltage produced by the voltaic reaction. The combustible analyzer induces an exothermic reaction in the region of a thermopile to produce a voltage difference along the length of the thermopile bearing a functional relationship to the concentration of a combustible element in the exothermic reaction. The conduit for routing the gas past the combustible element analyzer includes a heating labyrinth for raising the temperature of the sample and a port for accessing air to be mixed with the sample. Also included in this combustible analyzer conduit is a pressure sensing device for maintaining proper calibration regardless of sample flow rate. The flow within the block is maintained by an aspirator operated by a pressure regulated compressed air source.

REEXAMINATION CERTIFICATE ISSUED UNDER 35 U.S.C. 307

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

AS A RESULT OF REEXAMINATION, IT HAS BEEN DETERMINED THAT:

Claims 1-5 and 7-11 are cancelled.

Claim 6 is determined to be patentable as amended.

New claim 12 is added and determined to be patentable.

6. The combustible fluid and oxygen concentration analyzer of claim 4 where said oxygen concentration analyzer comprises:
   a. a reactor member;
   b. a heater element, *configured in the form of a mesh structure,* embedded within said reactor member; and
   c. a base for mounting said reactor member;
   d. said reactor member comprising:
      i. an electrolyte with oxygen ion vacancies providing paths for oxygen ion conduction;
      ii. a first and second conductive electrode for inducing a voltaic reaction within said source, and
      iii. means for connecting said first and second conductive electrodes to external means for measuring the voltage difference created in said electrodes by said voltaic reaction.

*12. The combustible fluid and oxygen concentration analyzer of claim 3 where said oxygen concentration analyzer comprises:*
   *a. a reactor member;*
   *b. a heater element, configured in the form of a mesh structure, embedded within said reactor member; and*
   *c. a base for mounting said reactor member;*
   *d. said reactor member comprising:*
      *i. an electrolyte with oxygen ion vacancies providing paths for oxygen ion conduction;*
      *ii. a first and second conductive electrode for inducing a voltaic reaction within said source, and*
      *iii. means for connecting said first and second conductive electrodes to external means for measuring the voltage difference created in said electrodes by said voltaic reaction.*

* * * * *